US005736394A

United States Patent [19]
Coleman et al.

[11] Patent Number: 5,736,394
[45] Date of Patent: Apr. 7, 1998

[54] CELLULAR UPTAKE OF MODIFIED PEPTIDES

[75] Inventors: Peter S. Coleman, Beverly Farms, Mass.; Katherine Sheldon, Nashua, N.H.

[73] Assignee: Boston Biomedical Research Institute, Boston, Mass.

[21] Appl. No.: 642,493

[22] Filed: May 3, 1996

[51] Int. Cl.⁶ .............................. C12N 5/00; C07K 5/00; C07K 7/00; C07K 17/00
[52] U.S. Cl. .................... 435/325; 530/330; 530/345; 436/64; 436/176; 435/173.1; 435/184; 435/963; 435/966
[58] Field of Search .................... 530/330, 345; 436/578, 579, 64, 176; 435/173.1, 184, 240.2, 240.1, 240.4, 963, 966, 325

[56] References Cited

U.S. PATENT DOCUMENTS 5,340,718   8/1994   Ullman et al. ........................ 435/6

OTHER PUBLICATIONS

Ying et al., *J. Biol. Chem.* 269: 470 (1994).
Prestwich et al., *DuPont Biotech Update:* 14 (Spring 1995).
Clack, James W., and Stein, Peter J., *J. Med. Chem.* 37: 2406 (1994).
Le Hir et al., *Laboratory Investigation* 73: 727 (1995).
Foxwell et al., *Molecular Pharmacology* 86: 543 (1989).
Andersen et al., *Insect Biochem. Molec. Biol.* 25: 713 (1995).
Adams et al., *Biochemistry* 34: 10553 (1995).
Nakamoto et al, *Biochemistry* 34: 10546 (1995).
Swindell et al., *J. Med. Chem.* 37: 1446 (1994).

*Primary Examiner*—Sheela Huff
*Attorney, Agent, or Firm*—Kevin M. Farrell

[57] ABSTRACT

Disclosed herein is a cell containing a modified peptide. More specifically, the N-terminal amino acid residue of the peptide is modified by the addition of an aryl ketone group which, when contacted with an appropriate substrate, and exposed to light having a wavelength of about 330 nm or greater, results in the covalent bonding of the peptide to the substrate by a C—H insertion dominant mechanism. In preferred, embodiments, the aryl ketone is a benzophenone moiety. The peptide can be designed to specifically bind to a protein of interest in the cell. The cell is then contacted with light having a wavelength of greater than about 330 nm to bind the peptide covalently to the binding site on the intracellular protein of interest. In this way, the modified peptide can be used to specifically and irreversibly block a binding site on an intracellular protein of interest.

24 Claims, 3 Drawing Sheets

CELLULAR UPTAKE OF MODIFIED PEPTIDES

BACKGROUND OF THE INVENTION

Cellular proteins function predominantly as enzymes. When considering the overall physiology and behavior of cells, intracellular enzyme activity can often be controlled, and a metabolic pathway can be regulated, by a variety of posttranslational modifications of the enzymes themselves. For example, protein kinase-catalyzed protein phosphorylations, or enzyme mediated covalent lipid modifications are found to occur at specific residues along an enzyme's primary sequence, and these alterations to protein structure change the physical characteristics and the activity profile of the enzyme. Therefore, inside the cell, the substrate of an enzyme often is another enzyme, with a particular enzyme's intracellular function depending on its having been previously operated on (and thereby activated or deactivated) through reaction with another enzyme. The control or regulation of enzyme activity by physical interactions between two or more enzymes plays a prominent role in programming the phenotype of cells. Many examples are known that involve a cascade of sequentially reacting enzymes (protein kinases and protein phosphatases) that regulate the activity of their enzyme substrates. Interest is currently very high in trying to clarify those multiple protein kinase cascades that transmit information from cell membrane receptors to the nucleus, a process referred to as signal transduction.

In vivo evidence of the specific roles played by any one member of a protein kinase signaling cascade, as an example, is not easy to acquire. Usually, such evidence is circumstantial and must be deduced indirectly. The current strategy usually involves the following steps. First, the investigator attempts to disrupt (interrupt) operation of a signaling cascade in vivo (i.e., in cell culture), either by genetic engineering, or by exposing cells to a chemical inhibitor of one of the enzymes in the signaling cascade. Then, a period of time must be allowed to elapse in order to observe a physiologic ("behavioral" or phenotypic) response of the affected cell (e.g., a change in motility, proliferation or differentiation). That the specific intracellular enzyme target has been affected by the experimental procedure in vivo must be verified by correlation with parallel data acquired from controlled enzyme assays in vitro, since the affected target enzyme cannot be directly identified in vivo. This inability to address, directly, a specified protein target site in vivo is a general one encountered in cell biology research. It is also a problem universally confronted in basic and applied research on potentially therapeutic pharmaceuticals, and is due mainly to the lack of site-directed, irreversible chemical tags that might be applied to living cells at the same time that an experimental manipulation of the targeted enzyme/protein is conducted.

If a broad spectrum of covalently binding (i.e., irreversible), target-selective ligands could be synthesized against various proteins (or other macromolecular targets), it would be possible to verify, directly and without the need for inference, intracellular protein—protein interactions within living cells. However, to synthesize such ligands, the following intermediate goals must be met:

covalently binding, target site-specific ligands for diverse proteins (or other macromolecules) must be synthesized;

their target selectivity first must be verified in vitro by means of competitive binding assays with similar compounds that are already known to bind reversibly to the suspected target molecule (such an assay must be available);

the covalently binding synthetic ligand must be assured of penetrating viable cells; and the covalently binding synthetic ligand must, itself, be experimentally identifiable (traceable) by means of a sensitive and readily available method (e.g., radioisotopic labeling).

SUMMARY OF THE INVENTION

The subject invention relates, in one aspect, to a cell containing a modified peptide. More specifically, the N-terminal amino acid residue of the peptide is modified by the addition of an aryl ketone group which, when contacted with an appropriate substrate, and exposed to light having a wavelength of about 330 nm or greater, results in the covalent bonding of the peptide to the substrate by a C—H insertion dominant mechanism. In preferred embodiments, the aryl ketone is a benzophenone moiety. The benzophenone moiety can be linked directly to the N-terminal amino acid via an amide linkage, or through a linker sequence. The modified peptide is designed to specifically bind to an intracellular target. The intracellular target can be, for example, an enzyme or other protein.

In another embodiment, the subject invention relates to a method for specifically and irreversibly blocking a binding site on an intracellular protein of interest. The method includes providing a peptide with an N-terminal modification as described above. The peptide is introduced into a cell which is known to contain the protein of interest. The cell is then contacted with light having a wavelength of greater than about 330 nm to bind the peptide covalently to the binding site on the intracellular protein of interest. This method is useful, for example, to inactivate a specific enzymatic activity.

In another embodiment, the present invention relates to a method for introducing a peptide of interest into a cell. The peptide is modified as described herein, and contacted with a cell under conditions appropriate for physiological activity. The experiments disclosed herein that the N-terminal modification facilitates cellular uptake of the peptide.

DETAILED DESCRIPTION OF THE INVENTION

The present invention is based on the discovery that peptides, bearing a specific modification, are taken up by living cells with high efficiency. This ability to introduce peptides into living cells represents a major advance in the art and facilitates functional studies which previously were not possible.

At least two significant problems have been recognized in the prior art which prevented such work in the past. First, it is known that peptides, which may be specific substrates or site-specific ligands for intracellular enzymes, resist penetration of the cell membrane. This impermeability of peptides into cells is due to several factors. For example, peptides are ionized molecules and thus do not readily diffuse across the non-polar hydrophobic lipid barrier of the plasma membrane. In addition, the presence of both extra- (in serum as well as on the cell surface) and intracellular (cytoplasmic) peptidases (exo- and endo-) rapidly degrade peptides added to cells in culture. Thus, even if a defined peptide sequence were to be taken in by viable cells, its intracellular half-life would be limited. Furthermore, the sequences of synthetic peptides that would prove capable of cellular uptake can only be assessed empirically. There are no a priori rules that, if followed, would ensure diffusion into cells of a diverse spectrum of varying peptide sequences.

A second significant problem relates to the fact that even if there were an efficient method developed for the uptake of a spectrum of enzyme-specific "native" peptides intracellularly, there exists no direct way for ascertaining the target selection of any such peptide within the cell. This difficulty is also confronted in almost all experimental work relating to drug delivery and the direct assay of target specificity in vivo.

Several attempts to overcome at least the first of the problems discussed above have been undertaken. For example, physically perturbing methods (permeabilizing cell membranes with "pore-forming" reagents, electroporation or microinjection) have been utilized. However, such methods can be either inefficient, harmful to cells, prone to inconsistent results, tedious or any combination of these.

Another attempt to overcome the problem of peptide uptake was based on synthesis of large (MW>5 kDa) branched peptides ("loligomers"), designed to contain membrane-translocating, nucleus-localizing signal sequences. However, even here, such specially defined "squid-like" peptide structures become internalized at physiologic temperature only over a period of hours by adsorptive endocytosis, which depends on cellular metabolism and the energetics required for plasma membrane endocytic vesicle formation, rather than on the non-metabolic, non-specific diffusion of the peptide through the membrane.

Another recent method relies on the synthetic construction of special chimeric peptides containing a previously identified signal peptide sequence known to allow lipid bilayer transit (e.g., the specific 16-mer AAVALLPAVLLA-LLAP SEQ ID NO: 1) coupled to a sequence that demonstrates specificity as a ligand for, say, a nuclear target protein.

The methods discussed above, even when demonstrated to be effective, are limited to those individual proteins or peptides empirically shown to be effective—they do not represent generally applicable solutions to the problem.

A fourth method, based on knowledge acquired in vitro of a peptide ligand's target-selective sequence, involves the design and synthesis of non-peptide, peptidomimetic organic molecules, whose structure and binding properties with their putative target enzyme/protein (or other macromolecules) permits them to transit the cell membrane. Once inside the cell, such analogues are not subject to proteolytic degradation. An example of this approach has been extremely successful for the selective targeting in vivo of only one key enzyme of protein—protein signaling involved in cell proliferation: farnesylprotein transferase (FPTase).

At least 6 different laboratories have synthesized non-peptide peptidomimetic proto-drugs which selectively inhibit FPTase in vitro. The analytical problems generated by these otherwise intriguing studies are manifest. The inhibition of intracellular FPTase activity with any of these peptidomimetic compounds is reversible. Thus, the intracellular target can only be deduced inferentially from parallel studies in vitro. Second, because these peptidomimetics do not irreversibly inactivate the enzyme, long-term inhibition may not be significant unless the proto-drug is constantly present. And third, the construction of different peptidomimetic enzyme inhibitors for a diverse set of different enzymes is a daunting and time-intensive task in organic synthesis.

In light of the problems identified above, the present method for introducing a peptide of interest into a cell represents a significant advance in the art. Although universal agreement on a definition for the term "peptides" does not exist, it is generally accepted that the term peptide applies to an amino acid polymer having a length of less than about 50 amino acid residues. In the experiments described below, peptides having a length of 5 amino acid residues been exemplified. In addition, similar results have been achieved using a peptide of 7 amino acid residues (APLTPGG SEQ ID NO: 2). Using no more than routine experimentation, one of skill in the art could determine the upper limit range which defines peptides falling within the scope of the present invention. One of skill in the art would predict with a high degree of certainty that peptides larger than those exemplified, when modified according to the present disclosure, would be taken up efficiently by living cells. However, routine experimentation would be required to determine an upper limit range with respect to molecular weight. While not wishing to be bound by prediction, it is likely that this upper limit will be substantially less than 50 amino acid residues (e.g., about 15–20 amino acids or less).

As indicated in the experimental section which follows, a highly basic peptide modified as described herein was not readily taken up by living cells. More specifically, the highly basic (3 Arg residues) MAP kinase substrate peptide, AP RTPGGRR SEQ ID NO: 3, gave no evidence for intracellular accumulation even at the relative high concentration of 48 µM. However, the experiments reported herein do demonstrate that neutral, hydrophobic or mildly acidic Bz-derivatized peptides were rapidly taken up by cells.

Peptides useful in connection with the present invention are characterized by ability to form a covalent bond when contacted with an appropriate substrate and exposed to light having a wavelength of about 330 nm or greater. The covalent bond with the substrate is formed by a C—H insertion dominant mechanism. Modifications of the peptide which confer this property are modifications in which an aryl ketone moiety is linked, preferably through an amide linkage, to the N-terminal residue of the peptide of interest.

Not all aryl ketone groups satisfy the criteria described in the preceding paragraph. A review of the literature coupled with routine experimentation will reveal useful groups. A preferred aryl ketone moiety is benzophenone, shown below.

The benzophenone moiety can be attached indirectly to the N-terminal amino acid via a linker sequence. For example, the benzophenone moiety could be coupled to a peptide of interest via a linker bearing either moderately flexible (1–3 CH$_2$ units, O, NH) or moderately rigid (C=O, COO functionalities).

Briefly, reviewing the reactivity of benzophenone, for example, absorption of a photon at about 350 nm results in the promotion of one electron from a nonbinding sp$^2$-like n-orbital on oxygen to an antibonding π*-orbital of the carbonyl group. In the diradicaloid triplet state, the electron-deficient oxygen n-orbital is electrophilic and therefore interacts with weak C—H σ-bonds, resulting in hydrogen abstraction to complete the half-filled n-orbital. When amines or similar heteroatoms are proximal to the excited carbonyl, an electron-transfer step may occur, followed by proton abstraction from an adjacent alkyl group and a radical 1,2-shift. The ketyl and alkyl radicals that are formed readily recombine to generate a new C—C bond, producing benzpinacol-type compounds. This basic process, which is also used for remote site functionalization, is based on the observation that the diradicaloid species can only attack geometrically accessible C—H bonds. The reactant and substrate must spend sufficient time at the interactive distance, thus furnishing the primary source of the site specificity.

In biological systems, the most effective H-donors include backbone C—H bonds in amino acids, polypeptides and carbohydrates. Methylene groups of lipids and amino acid side chains also provide abstractable hydrogens. In the absence of any orientational preference, the reactivity order for C—H bonds is:

>NCH$_x$—SCH$_y$>methine>C=CCH$_2$>—CH$_2$—>—CH$_3$.

Particularly reactive sites include the electron-rich tertiary centers such as C$_\gamma$—H and C$_\beta$—H of valine and those CH$_2$ groups adjacent to heteroatoms in Lys, Arg and Met.

The term "benzophenone moiety" as used herein, is intended to encompass derivatives of benzophenone which are useful in connection with the present invention. Therefore, as used herein, the term benzophenone moiety means benzophenone or substitutions thereof which do not substantially detract from the of benzophenone in a hydrogen abstraction-type reaction, either electronically, or sterically. One of skill in the art will recognize that such considerations apply also to other aryl ketone functionalities identified as previously described, Electron-withdrawing groups increase the efficiency of hydrogen-abstraction. Electron-donating groups and electron delocalization into aromatic and conjugated systems cause a partial shift of the electron transition from n-π* to π-π*, and the latter triplet state becomes much less reactive toward hydrogen-abstraction. The overall quantum yield (Φ) varies from 0.05 to 0.4, with the higher values for the simple n-π* transition.

With respect to steric accessibility, it is known that benzophenone substituents can play a role. The placement of alkyl groups in ortho or meta positions of the benzophenone increases the probability of intramolecular interactions that reduce effectiveness.

The modified peptides disclosed herein can be introduced into any type of cell, be it prokaryotic or eukaryotic, provided that the concentration of the modified peptide in the local environment of the cell can be brought to a sufficiently high level. Routine experimentation will be required to determine the minimum extracellular level required. This will, of course, be to some extent dependent upon the "specific activity" of the peptide with respect to its target. When considering a whole organism (e.g., a human patient), circulating cells would be anticipated to be particularly attractive targets. However, a priori, no tissue type would be excluded as a target for therapy.

The compositions of the present invention can be used in connection with a variety of methods, both in vivo and in vitro. For example, the activity any enzyme having a catalytic domain known to bind to a particular substrate domain can be specifically inhibited. If the enzyme carries out an essential cellular function, the result will be cell death. The intracellular target need not be an enzyme. The compositions and methods of the present invention are applicable to any protein/protein or protein/macromolecule interaction. In fact, the compositons and methods of the present invention are applicable to the interaction of any specific binding pair wherein a first member is an amino acid polymer and the second member binds specifically to the first member such that a hydrogen-abstraction reaction of the type described above can take place upon photoactivation.

In a particular ex vivo embodiment, for example, a bone marrow culture explant of a leukemia patient is obtained. The methods of the present invention can be used to selectively eliminate leukemic cells from a sample of the patient's bone marrow (for subsequent reinfusion) without perturbing the marrow's normal cells.

A high-dose chemotherapy with bone marrow stem cell rescue is, at present, a standard, and sometimes curative, treatment for a variety of cancers, including leukemias, lymphomas, and, more recently, glioblastomas and other metastatic solid tumors. A common step in all of the current stem cell-rescue protocols involves withdrawing a portion of the patient's bone marrow prior to the marrow-ablating chemotherapy. The resulting short-term in vitro culture of the marrow cells is then treated to eliminate, if possible, any malignant cells present in it before the reinfusion of the purged bone marrow back to the patient whose resident bone marrow has been ablated by a high-dose chemotherapy.

The current methods for selectively killing malignant cells in the marrow cell culture involve treatments with conventional chimeric toxins (Vitetta et al., Imm. Today 14: 252 (1993)), which comprise a cytotoxic effector domain and a domain (typically antibody-based) that binds to a structure on the surface of target cells. This design of chimeric toxins is often, but not always, sufficient for eliminating most leukemic cells (the bulk of which bears lineage-specific surface markers) from an explant culture of a bone marrow. Unfortunately, many types of tumor cells, including nonhematologic cancers, are much more heterogeneous, surface marker-wise, than certain types of leukemias. Therefore a complete, assured and selective elimination of metastic tumor cells from an in vitro culture of bone marrow prior to its reinfusion remains, in general, a problem to be solved.

By contrast, the methods and compositions of the present invention, by virtue of their selectivity and sensitivity to intracellular targets (as distinguished from cell surface ones) will provide an alternative and more selective means for in vitro bone marrow purging of cancer cells.

For example, HL60 is a human leukemia cell line which is dependent upon a mutated ras gene product for growth. Normal bone marrow cells contain a normal ras gene product, and are less dependent upon the ras gene product for their growth. Therefore, specific inhibition of the ras gene product by the methods disclosed herein will be lethal for leukemic cells, and non-lethal for normal leukemic cells. The treatment of a bone marrow explant offers particular advantages for use in connection with the methods of the present invention in light of the need to exposure to light of an appropriate wavelength. Although it is possible to introduce an appropriate light emitting source into many areas of the body of a whole organism such as a human patient, a non-invasive approach is preferred. Specific killing of leukemic cells followed by reinfusion into a cancer patient is technically straight forward technique.

One of skill in the art would be able to identify numerous intracellular targets of interest, for example, in connection with disease therapy. Ligands for many of these targets will be known at the epitope level. In addition, identification of a ligand epitope specifically recognized by an intracellular protein of interest can be identified by the now routine technique referred to as "biopanning" which employs an epitope library expressing fusion proteins which containing billions of different epitopes (see e.g., Smith and Scott, Meth. Enzymol. 217: 228 (1993)). A solution containing such fusion proteins can be passed over a solid support to which the intracellular protein of interest is attached. The support is washed and specifically bound peptides are eluted, and their amino acid sequence determined using well known techniques.

In addition to applications which exploit the covalent bond-forming characteristic of the aryl ketone modified peptides, the subject disclosure demonstrates that the modified peptides cross the cell membrane efficiently. One of skill in the art will recognize applications for peptide introduction in which covalent cross-linking to a substrate would be unnecessary or undesirable. The fact that modifications of the type described herein are useful for introducing a peptide into a cell, is useful apart from the covalent bonding embodiments of the present invention which require photo-activation.

EXEMPLIFICATION i) Cellular Uptake of Bz-peptides

A Bz-derivatized pentapeptide Bz-ACVIM SEQ ID NO: 4, as shown below, was synthesized by means of a solid-phase, automated synthetic method. The peptide was built by tethering its C-terminus to a bead structure and adding subsequent amino acids to the N-terminus. 4-benzoylbenzoic acid, after appropriate activation of the 4-carboxyl function, is reacted with the bead-tethered peptide to couple, by an amide bond, the benzophenone moiety to the peptide's N-terminus. The signature sequence -CVIM is known to bind specifically directed to the catalytic site of the enzyme farnesylprotein transferase (FPTase).

medium at 37° C. together with either [$^3$H]-benzoylbenzoic acid ([$^3$H]BBA) or the [$^3$H]Bz-peptide over a 45 min time course. Aliquots (0.5 mL) of the cell suspension were removed at the times shown and separated from the aqueous medium by centrifugation through a silicone oil barrier. The cell pellets in the oil layer were counted. The data (only those for Bz-ACVIM SEQ ID NO: 4 are shown; Bz-ACVIL SEQ ID NO: 5 behaved similarly) indicate that the influx and equilibration of the Bz-peptides were extremely rapid, reaching maximum levels within 15 min. Any difference in influx rates between BBA and Bz-ACVIM SEQ ID NO: 4 could be due to both the larger size of the Bz-peptide, and the slight negative (C-terminus) charge carried by the latter.

Figure 1A:
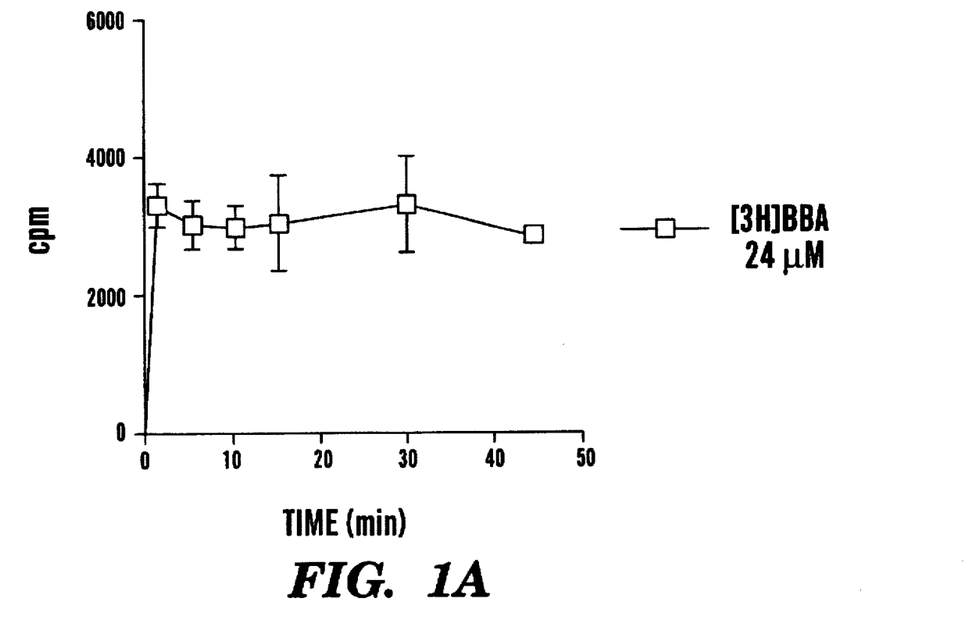
FIGS. 1A and 1B are a diagrammatic representation depicting A) uptake of [³H]BBA by HL60 cells, and B) uptake of [³H]Bz-ACVIM SEQ ID NO: 4 by HL60 cells.

More specifically, Bz-ACVIM SEQ ID NO: 4 displayed rates of penetration (at 24 μM) almost identical to that for the uptake of [$^3$H]BBA itself, which is not a site-specific ligand for any enzyme. These preliminary uptake data, without photolysis, are shown in FIGS. 1A ([$^3$H]BBA uptake) and 1B ([$^3$H]Bz-ACVIM SEQ ID NO: 4 uptake). The lowest trace in FIG. 1B also demonstrates that the presence of an N-terminus Bz moiety cannot guarantee cellular uptake of any peptide; the highly basic (3 Arg residues), MAP kinase substrate peptide, APRTPGGRR SEQ ID NO: 3, gave no evidence for intracellular accumulation even at the relative high concentration of 48 μM.

Figure 1B:
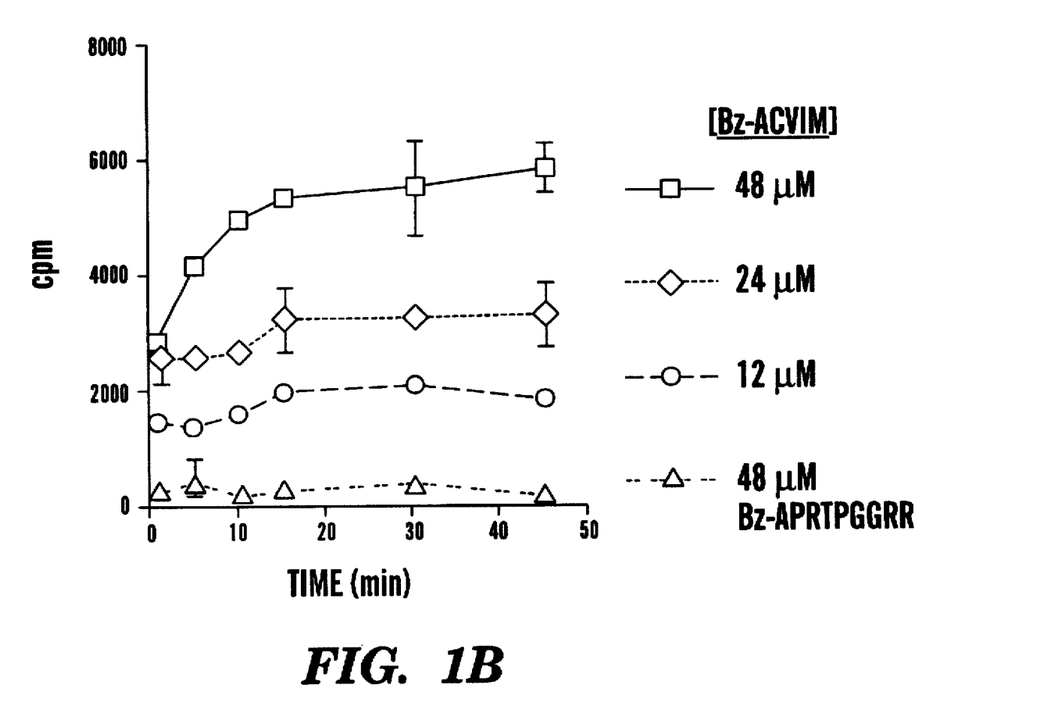
Figure 2A:
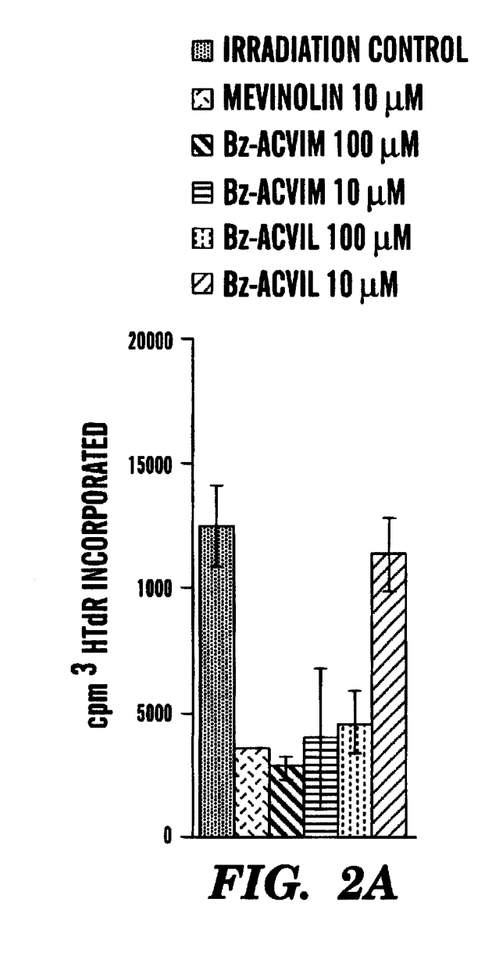
FIGS. 2A and 2B are diagrammatic representations depicting inhibition of HL60 cell proliferation induced by photolysis of intracellular Bz-ACVIM SEQ ID NO: 4 and Bz-ACVIL SEQ ID NO: 5.
Figure 2B:
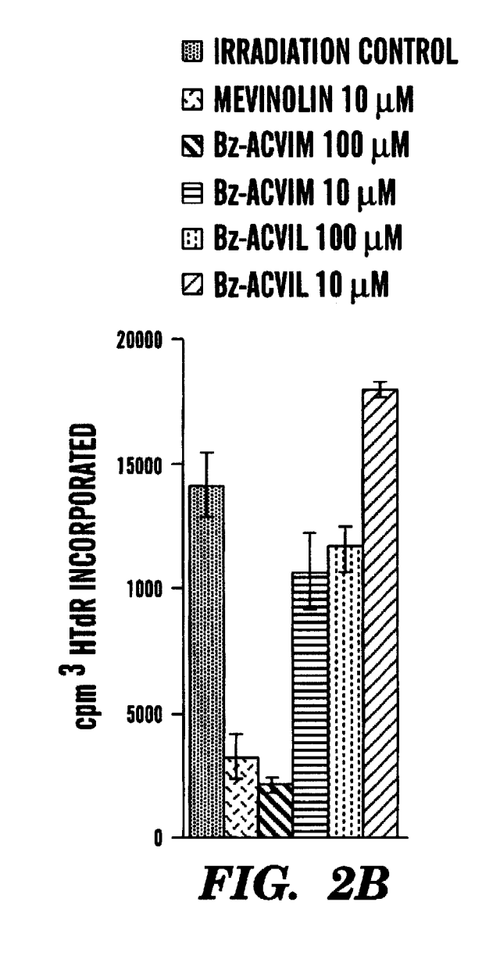

The data imply that Bz-ACVIM/L SEQ ID NOS: 4 and 5 are able to freely cross membranes and, according to rough calculations, may even accumulate within the cell relative to the external milieu, over time. This conclusion is based on the following assumptions. The volume of an average HL60 cell can be estimated as $4.2 \times 10^{-6}$ μL. Thus, the pellet volume occupied by a 0.5 μL suspension of $10^6$ cells is ~4 mL. The radioactivity contained in the sample of [$^3$H]Bz-peptide for the 12 μM incubation=100 cpm/μL. Consequently, the maximum concentration of peptide in the cell pellet should be equivalent to ~400 cpm. FIG. 1B indicates, however, that for the 12 μM Bz-ACVIM SEQ ID NO: 4 incubation, ~4 times more than the expected cpm have accumulated intracellularly. This suggests that intracellular interactions can occur which alter the equilibrium between intra- and extra-cellular Bz-peptide. Of course, the rough calculations depend on cell volume (pellet volume) estimates. However, the inescapable conclusion from FIG. 1B is that neutral, hydrophobic or mildly acidic Bz-derivatized peptides are rapidly taken into cells.

ii) Photolytic Activation of Intracellular Bz-ACVIM and Bz-ACVIL Inhibits Tumor Cell Proliferation Initial experiments were designed to determine whether the Bz-modified peptide could cross cellular membranes. The methods employed for these studies are given briefly. First, $2 \times 10^6$ HL-60 cells/mL were incubated in serum free Experiments were designed to determine whether, after admission of the target-specific Bz-peptide molecules into proliferating cells, their photolysis in situ would induce a cytostatic response. Such a response would implicate the irreversible inhibition of ras-prenylating enzymes. FIG. 2A,B displays results from several trials employing Bz-ACVIM SEQ ID NO: 4 and Bz-ACVIL SEQ ID NO: 5, the in vitro-specific photoaffinity inhibitors of FPTase and GGPTase-I, respectively. It is important to note that, regardless of treatment, Trypan blue-assessed viability remained above 90% under the conditions employed for all experiments shown in FIG. 2A,B.

Two fundamental variations were performed. For FIG. 2A, cells were incubated in serum-free medium in the presence of a Bz-peptide, mevinolin, or, as control, with the DMSO delivery vehicle alone, for 15 min at room temp., after which fetal bovine serum was added to 10% (v/v) followed by plating in triplicate at 0.5 mL/well. These plates were immediately irradiated at 365 nm for 15 min to excite the intracellular Bz photophore, then placed in the incubator at 37° C. for 24 h. For FIG. 2B, the same procedure was followed except that, after serum replenishment and plating, cells were first incubated at 37° C. for 1 h, then removed from the incubator, irradiated for 15 min, and returned to incubation for 24 h. The 1 h incubation prior to irradiation was performed to assess, indirectly, the potential for intracellular destruction (or other means of depletion) of the Bz-peptides. At 24 h after serum replenishment, all cells were pulse-labeled with [$^3$H]TdR to record the effect of intracellular Bz-peptide photolysis (as well as of mevinolin treatment, the effects of which have been well documented) on DNA synthesis and, thereby, on cell proliferation.

The data in both FIGS. 2A and B clearly reveal no deleterious effect of low energy irradiation upon HL60 cells in the absence of added antimetabolites (Irradiation Control, left bar, FIGS. 2A & 2B). Moreover, the cellular response of growth inhibition by 10 μM mevinolin (2nd bar from left, FIGS. 2A & B) was apparent regardless of whether irradiation was delayed for 1 h or not. Mevinolin, a reversible competitive inhibitor of HMGR, is known to block synthesis of isoprenoid intermediates of the cholesterol pathway and is not photoreactive. Depletion of intracellular isoprenoid intermediates by mevinolin thereby prevents farnesylation of p21$^{ras}$, interrupts its participation in signal transduction, and cell proliferation is blocked. The mevinolin response in these experiments serves as an excellent comparative control for cell growth inhibition resulting from a mechanism that lies distal to the ras/Raf-triggered signal transduction events.

FIG. 2A shows that the effects of in situ photolysis of the FPTase inhibitor Bz-ACVIM SEQ ID NO: 4, at both 10 μM and 100 μM, are dramatic. Upon irradiation immediately after plating, both 100 μM (3rd bar from left) and 10 μM (4th bar from left) Bz-ACVIM SEQ ID NO: 4 induce inhibition of DNA synthesis (by ~75–80%), and therefore of cell growth (verified by diminished cell counts), at least as effectively as mevinolin (2nd bar from left). Furthermore, seemingly congruent with recently proposed indications for cross-prenylation of the ras homolog TC21, it was observed that the GGPTase-I-specific Bz-ACVIL SEQ ID NO: 5 at 100 μM (5th bar from left) effected a clear cytostatic response, but did not do so when the concentration had been reduced to 10 μM (6th bar from left).

FIG. 2B manifests similarly intriguing results that, due to the slightly different protocol used (a 1 h delay prior to photolysis) serves to reinforce the conclusions drawn from FIG. 2A. In FIG. 2B it can be seen that the cytostatic effect of 100 μM Bz-ACVIM SEQ ID NO: 4 (3rd bar from left) remained at least as powerful as in FIG. 2A. However, a reduced concentration of this irreversible FPTase photoinhibitor (10 μM; 4th bar from left)) had a much lower inhibitory effect relative to the response obtained in FIG. 2A. Similarly, due to the 1 h delay before photolysis, the GGPTase-I-specific inhibitor, Bz-ACVIL SEQ ID NO: 5, at 100 μM, lost about 60% of the inhibitory capacity made manifest in FIG. 2A (5th bar from left), while at the lower concentration (10 μM), Bz-ACVIL SEQ ID NO: 5 was ineffective.

iii) Relative In Vivo Stability of Bz-peptide-induced Inhibition of Prenylprotein Transferase-mediated Cell Proliferation A set of experiments were designed to assess the effects of Bz-peptides on ras-mediated signaling of cell proliferation, under conditions where incubations of cells, post peptide addition, were shorter (18 h) than that found optimal for their population doubling (~24 h). Experiments were intended to reveal early differences in the relative stability of the Bz-peptides, as judged by their effects on inhibition of cell proliferation, plus or minus irradiation. It was also necessary to clearly demonstrate that BBA itself has no effect on cell proliferation.

HL60 cells were exposed to Bz-ACVIM SEQ ID NO: 4 (FPTase-specific), Bz-ACVIL SEQ ID NO: 5 (GGPTase-I-specific), the benzophenone photophore (BBA), mevinolin (proliferation inhibition control), or the DMSO vehicle alone, plus or minus irradiation. After incubation for 18 h at 37° C., irradiated and non-irradiated cultures were assayed for [$^3$H]TdR incorporation into DNA (a measure of proliferation).

Both panels (FIGS. 3a and 3b) demonstrate that 100 μM Bz-peptide causes dramatic inhibition of cell proliferation, whereas 10 μM is ineffective, regardless of cell irradiation. However, the right panel illustrates that, without irradiation, the beginning of a "recovery" of proliferation of cells exposed to the Bz-peptides is evident, implying that during the 18 h incubation the intracellular level of these Bz-peptides has begun to diminish, perhaps due to proteolysis (or other means of their destabilization). These data imply that the photolysis of intracellular Bz-peptide (left panel), which putatively effects their covalent binding to the prenylprotein transferases, irreversibly inhibits these targeted enzymes in vivo, whereas under conditions of a reversible association between the Bz-peptides and their targeted enzymes (right panel), the time-dependent loss of the biological effect is evident as early as 18 h after exposure of cells to the Bz-peptides.

Figure 3A:
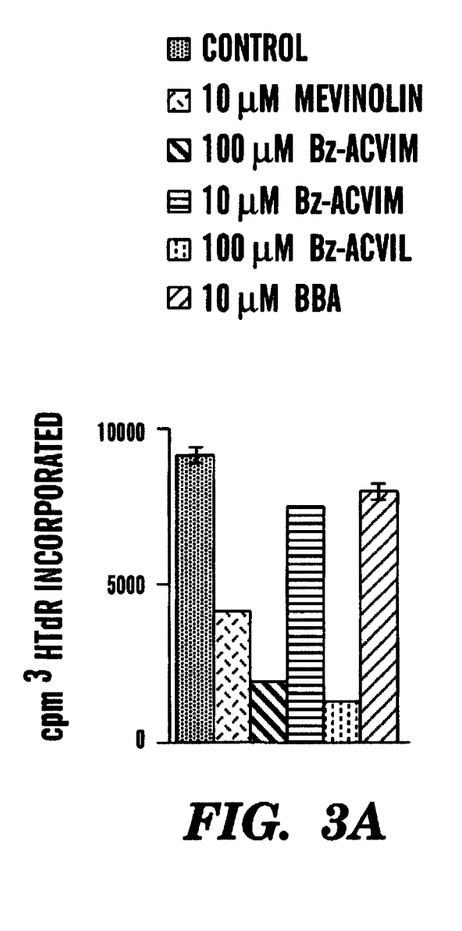
FIG. 3 is a diagrammatic representation depicting relative in vivo stability of Bz-peptide induced inhibition of prenyl-protein transferase-mediated cell proliferation.
Figure 3B:
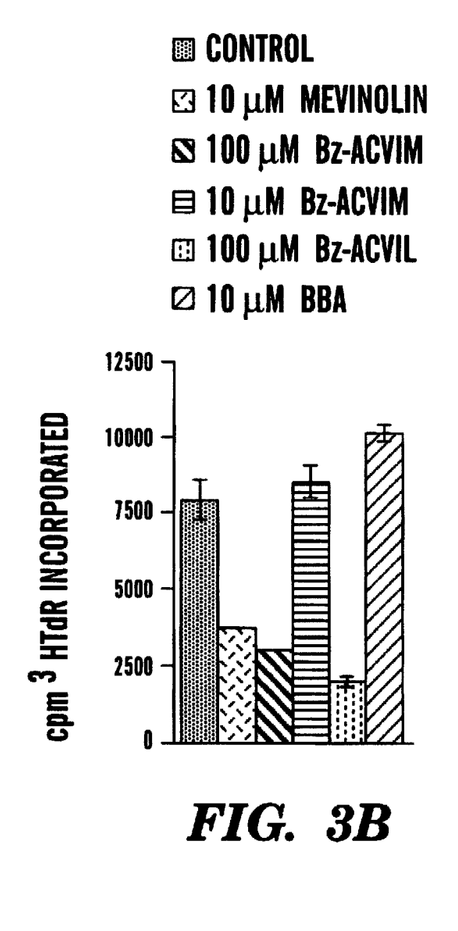

It is especially noteworthy that intracellular accumulation of the benzophenone photophore (BBA) itself, whether cells were irradiated or not, showed no effect regarding the cell's capacity for proliferation (6th bar, both panels). This critical result strongly supports the target specificity of intracellular Bz-peptides, and eliminates, as a cause of cell growth inhibition, any non-specific covalent binding to random macromolecules in vivo of benzophenone by itself. In addition, the relative extent of inhibition of cell proliferation caused by mevinolin (2nd bar, both panels) remained constant (~50%), whether or not cells were irradiated, verifying that effects due to the presence of mevinolin are independent of cell irradiation.

We claim:

1. A biological cell containing an intracellular peptide, the amino terminus of the N-terminal amino acid residue of the peptide being modified by the addition of an aryl ketone group which, when contacted with an electron donating substrate, and exposed to light having a wavelength of about 330 nm or greater, results in the covalent bonding of the peptide to the substrate.

2. The biological cell of claim 1 wherein the aryl ketone is a benzophenone moiety.

3. The biological cell of claim 2 wherein the benzophenone moiety is linked to the N-terminal amino acid via a linker sequence.

4. The biological cell of claim 3 wherein the benzophenone moiety is linked to the N-terminal amino acid via a carboxyl group on the benzophenone to form an amide linkage with the N-terminal amino acid of the peptide.

5. The biological cell of claim 2 wherein the electron donating substrate is an intracellular target protein.

6. The biological cell of claim 5 wherein the biological cell is a tumor cell.

7. The biological cell of claim 6 wherein the intracellular target protein is the ras gene product.

8. The biological cell of claim 7 wherein the amino acid sequence of the peptide is ACVIM (SEQ ID NO: 4).

9. A method for specifically and irreversibly blocking a binding site on an intracellular protein of interest, the method comprising:

a) providing a peptide which binds the binding site of the protein of interest, the amino terminus of the N-terminal amino acid residue of the peptide being modified by the addition of an aryl ketone group;

b) introducing the peptide of step a) into a biological cell containing the protein of interest; and c) contacting the biological cell of step b) with light having a wavelength of greater than about 330 nm to bind the peptide covalently to the binding site on the intracellular protein of interest.

10. The method of claim 9 wherein the aryl ketone is a benzophenone moiety.

11. The method of claim 10 wherein the benzophenone moiety is linked to the N-terminal amino acid via a linker sequence.

12. The method of claim 11 wherein the benzophenone moiety is linked to the N-terminal amino acid via a carboxyl group on the benzophenone to form an amide linkage with the N-terminal amino acid of the peptide.

13. The method of claim 10 wherein the peptide binds specifically to the intracellular protein.

14. The method of claim 13 wherein the biological cell is a tumor cell.

15. The method of claim 14 wherein the intracellular target protein is the ras gene product.

16. The method of claim 15 wherein the amino acid sequence of the peptide is ACVIM (SEQ ID NO: 4).

17. A method for introducing a peptide into a biological cell, the method comprising:

a) providing the peptide, the amino terminus of the N-terminal amino acid residue of the peptide being modified by the addition of an aryl ketone group which, when contacted with a binding site on an intracellular protein of interest, and exposed to light having a wavelength of about 330 nm or greater, results in the covalent bonding of the peptide to the binding site on the protein of interest; and b) contacting the peptide of step a) with a biological cell, under conditions appropriate for physiological activity.

18. The method of claim 17 wherein the aryl ketone is a benzophenone moiety.

19. The method of claim 18 wherein the benzophenone moiety is linked to the N-terminal amino acid via a linker sequence.

20. The method of claim 19 wherein the benzophenone moiety is linked to the N-terminal amino acid via a carboxyl group on the benzophenone to form an amide linkage with the N-terminal amino acid of the peptide.

21. The method of claim 18 wherein the peptide binds specifically to the intracellular protein of interest.

22. The method of claim 21 wherein the biological cell is a tumor cell.

23. The method of claim 22 wherein the intracellular target protein is the ras gene product.

24. The method of claim 23 wherein the amino acid sequence of the peptide is ACVIM (SEQ ID NO: 4).

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 16 amino acids
      ( B ) TYPE: amino acid
      ( C ) STRANDEDNESS: single
      ( D ) TOPOLOGY: linear    ( i i ) MOLECULE TYPE: peptide    ( x i ) SEQUENCE DESCRIPTION: SEQ ID NO:1:

```
Ala  Ala  Val  Ala  Leu  Leu  Pro  Ala  Val  Leu  Leu  Ala  Leu  Leu  Ala  Pro
 1              5                        10                      15
```

( 2 ) INFORMATION FOR SEQ ID NO:2:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear    ( i i ) MOLECULE TYPE: peptide    ( x i ) SEQUENCE DESCRIPTION: SEQ ID NO:2:

```
Ala  Pro  Leu  Thr  Pro  Gly  Gly
 1              5
```

( 2 ) INFORMATION FOR SEQ ID NO:3:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear    ( i i ) MOLECULE TYPE: peptide    ( x i ) SEQUENCE DESCRIPTION: SEQ ID NO:3:

```
Ala  Pro  Arg  Thr  Pro  Gly  Gly  Arg  Arg
 1              5
```

( 2 ) INFORMATION FOR SEQ ID NO:4:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear    ( i i ) MOLECULE TYPE: peptide    ( x i ) SEQUENCE DESCRIPTION: SEQ ID NO:4:

```
Ala  Cys  Val  Ile  Met
 1              5
```

( 2 ) INFORMATION FOR SEQ ID NO:5:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:5:

Ala Cys Val Ile Leu
1               5